US00PP34926P2

(12) United States Plant Patent
Smith

(10) Patent No.: US PP34,926 P2
(45) Date of Patent: Jan. 17, 2023

(54) ***CHRYSANTHEMUM* PLANT NAMED 'CIFZ0097'**

(50) Latin Name: *Chrysanthemum x morifolium*
Varietal Denomination: CIFZ0097

(71) Applicant: SYNGENTA CROP PROTECTION AG, Basel (CH)

(72) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/580,784

(22) Filed: Jan. 21, 2022

(51) Int. Cl.
*A01H 5/02* (2018.01)
*A01H 6/14* (2018.01)

(52) U.S. Cl.
USPC ..... Plt./293
CPC ..... *A01H 6/1424* (2018.05)

(58) Field of Classification Search
USPC ..... Plt./293
CPC ..... A01H 6/1424
See application file for complete search history.

*Primary Examiner* — Anne Marie Grunberg
(74) *Attorney, Agent, or Firm* — Dale Skalla

(57) ABSTRACT

A new garden type *Chrysanthemum* plant named 'CIFZ0097' particularly distinguished by its medium size plant with round plant habit, small sized decorative flowers with red flower color, and a natural season response early to mid-September.

1 Drawing Sheet

Figure 1:
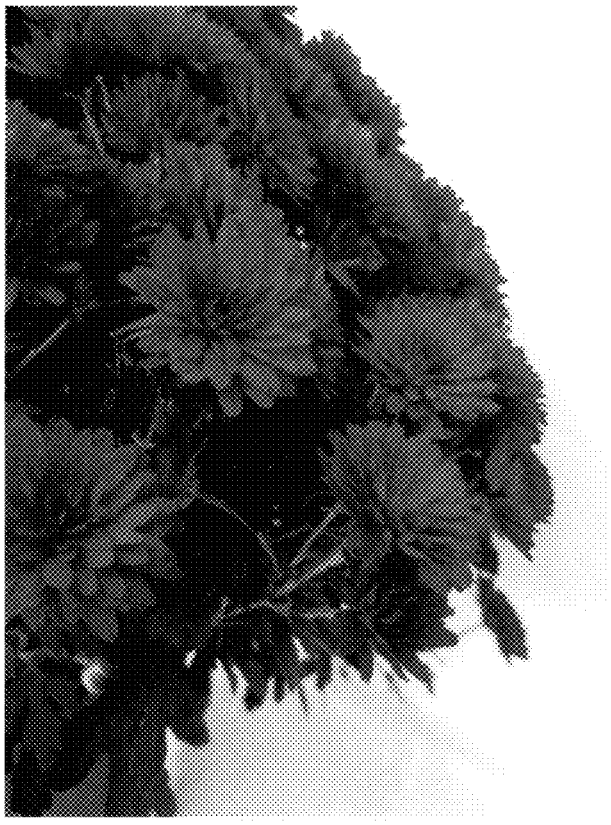

Latin name of the genus and species of the plant claimed: *Chrysanthemum* x *morifolium.*

Varietal denomination: 'CIFZ0097'.

BACKGROUND OF THE NEW PLANT

The present invention comprises a new *Chrysanthemum*, botanically known as *Chrysanthemum* x *morifolium*, and hereinafter referred to by the variety name 'CIFZ0097'.

'CIFZ0097' is a product of a planned breeding program. The new cultivar has a medium sized plant with round plant habit, small sized decorative flowers with red flower color, and a natural season response early to mid-September.

'CIFZ0097' originated from a cross made in September 2017 in Enkhuizen, The Netherlands. Seeds were sown in June 2018 in Gilroy, Calif. and 'CIFZ0097' was selected from the resulting population on Nov. 5, 2018 in Alva, Fla.

The female parent was 'CIFZ0058', U.S. Plant Pat. No. 29,804

TABLE 1

Characteristics of the female parent, compared to 'CIFZ0097':

| Trait | 'CIFZ0097' | 'CIFZ0058' |
|---|---|---|
| Natural response: | 1 week slower | 1 week faster |
| Blackcloth response: | ½ week slower | ½ week faster |
| Flower size: | Similar or bit smaller | Similar or bit larger |
| Flower color: | Red | Purple |
| Flower type: | Similar | Similar |
| Plant size: | Larger | Smaller |
| Plant habit: | Fuller, shorter peduncles | More gaps in canopy from longer peduncles |
| Flower longevity: | Flowers last but color fades | Flowers and color hold up |
| Flowering uniformity: | More uniform | Less uniform |

The male parent was 'CIFZ0060', U.S. Plant Pat. No. 31,512

TABLE 2

Characteristics of the male parent, compared to 'CIFZ0097':

| Trait | 'CIFZ0097' | 'CIFZ0060' |
|---|---|---|
| Natural response: | 1 week faster | 1 week slower |
| Blackcloth response: | ½ week slower | ½ week faster |
| Flower size: | Smaller | Larger |
| Flower color: | Lighter red | Darker red |
| Flower type: | Similar | Similar |
| Plant size: | Less width | Wider |
| Plant habit: | Similar | Similar |
| Flower longevity: | Similar | Similar |
| Plant strength: | Stronger peduncles | Weaker peduncles |

The first act of asexual reproduction of 'CIFZ0097' was accomplished when vegetative cuttings were propagated from the initial selection in January 2019 in Alva, Fla.

BRIEF SUMMARY OF INVENTION

Horticultural examination of plants grown from cuttings of the plant initiated in January 2019 and continuing thereafter, has demonstrated that the combination of characteristics as herein disclosed for 'CIFZ0097' are firmly fixed and are retained through successive generations of asexual reproduction.

'CIFZ0097' has not been observed under all possible environmental conditions. The phenotype may vary significantly with variations in environment such as temperature, light intensity and day length.

A Plant Breeder's Right for this cultivar has not yet been applied for. 'CIFZ0097' has not been made publicly available prior to the effective filing date of this application, notwithstanding any disclosure that may have been made less than one year prior to the effective filing date of this application by the inventor or another who obtained 'CIFZ0097' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical flower and foliage characteristics of 'CIFZ0097' with colors being as true as possible with an illustration of this type. The photographic drawings show in FIG. 1 a close view of flower of the new variety and in FIG. 2 a flowering plant from an outdoor trial.

Figure 2:
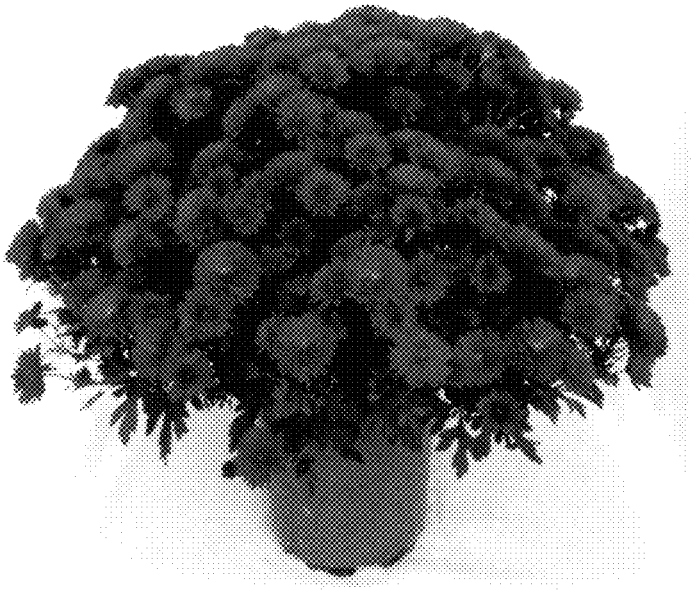

The aforementioned photographs: FIG. 1, as well as FIG. 2 were taken on Sep. 8, 2021 both showing a plant from the same blackcloth outdoor trial in Enkhuizen, The Netherlands.

These plants were about 13 weeks of age. One rooted cutting per pot had been planted in a 19 cm pot, not pinched in week 23, 2021 and black clothed from week 29. Plants started flowering the end of August 2021.

The measurements were taken in Enkhuizen, The Netherlands, in September, 2021 on plants from the same outdoor blackcloth trial.

DETAILED BOTANICAL DESCRIPTION

Color references are made to The Royal Horticultural Society Colour Chart (R.H.S.) 2001.

DIFFERENCES BETWEEN THE NEW VARIETY 'CIFZ0097' AND TWO MOST SIMILAR VARIETIES

TABLE 3

| Trait | 'CIFZ0097' | 'Yobonnie', U.S. Plant Pat. No. 18,886 |
|---|---|---|
| Natural response: | Similar | Similar |
| Blackcloth response: | ½ week slower | ½ week faster |
| Flower size: | Smaller | Larger |
| Flower color: | Lighter red | Darker red |
| Flower type: | Decorative-less disc florets | Daisy-more disc florets |
| Plant size: | Similar | Similar |
| Flower longevity: | Flowers lasts 20% longer | Flowers last 20% less time |
| Foliage: | Paler green | Darker green |
| Flowering uniformity: | More uniform | Less uniform |

TABLE 4

| Trait | 'CIFZ0097' | 'Granata Red', U.S. Plant Pat. No. 23,135 |
|---|---|---|
| Natural response: | ½ week faster | ½ week slower |
| Blackcloth response: | ½ week slower | ½ week faster |
| Flower size | Smaller | Larger |
| Flower color: | Lighter red | Darker red |
| Flower type: | Similar | Similar |
| Plant size: | Smaller overall | Larger overall |
| Plant habit: | Rounder | More upright |
| Flower longevity: | Flower color lasts 20% longer | Flowers last 20% less time |
| Foliage: | Paler green | Darker green |
| Flowering uniformity: | More uniform | Less uniform |

Plant:

*Form, growth and habit.*—Herbaceous garden-type, stems Upright and outwardly spreading, freely branching, strong and moderately vigorous growth habit.

*Plant height* (*above soil*).—25 cm.

*Plant height* (*inflorescence included*).—28 cm.

*Plant width.*—49 cm.

Roots:

*Number of days to initiate roots.*—About 4 days at about 22° C.

*Number of days to produce a rooted cutting.*—14-16 days at 22° C.

*Type.*—Fine, fibrous, free branching.

*Color.*—RHS N155B.

Foliage:

*Arrangement.*—Alternate.

*Immature leaf, color upper surface.*—RHS 137B.

*Immature leaf, color lower surface.*—RHS 137C.

*Mature leaf, color, upper surface.*—RHS 139A.

*Mature leaf, color lower surface.*—RHS 137A.

*Length.*—8 cm.

*Width.*—4.5 cm.

*Shape.*—Ovate, with distinct lobes.

*Base shape.*—Attenuate.

*Apex shape.*—Acute.

*Margin.*—3 to 4-lobed.

*Number of margin indentations.*—Approximately 12.

*Depth of margin indentations.*—2-3 mm.

*Leaf length terminal lobe relative to total leaf length.*—1:1/7.

*Leaf depth lower lateral sinus.*—1.0 cm.

*Texture, upper surface.*—Smooth, occasionally bifid hairs.

*Texture, lower surface.*—Bifid hairs.

*Color of veins, upper surface.*—RHS 147B.

*Color of veins, lower surface.*—RHS 147B.

*Pattern of veining.*—Palmate.

*Petiole color.*—RHS 147B.

*Petiole length.*—2.0 cm.

*Diameter.*—0.3 cm.

*Texture.*—bifid hairs.

*Presence of stipules.*—Not present.

Stem:

*Quantity of main branches per plant.*—8.

*Color of stem.*—RHS 147B.

*Length of stem.*—12-14 cm.

*Diameter.*—0.5 cm.

*Length of internodes.*—1.5-3.0 cm.

*Texture.*—Bifid hairs.

*Color of peduncle.*—RHS 147B.

*Length of peduncle.*—2.5-3.5 cm.

*Peduncle diameter.*—0.2 cm.

*Texture.*—Bifid hairs.

Inflorescence:

*Type.*—Compositae, solitary, decorative type inflorescences borne terminally above foliage, ligulate ray florets arranged in whorls on a capitulum giving a double flower with some disc florets in the center of the flower.

*Quantity of short days to flowering* (*response time*).—Approximately 7 weeks.

*Quantity of inflorescences per plant.*—270 with some buds developing.

*Lastingness of individual blooms on the plant*.—About 4.5 weeks from first color.
*Fragrance*.—Slightly spicy.

Bud (when showing color):
*Color*.—RHS 59A.
*Length*.—1 cm.
*Width*.—0.7 cm.
*Shape*.—Oblate.

Immature inflorescence (at moment of opening):
*Diameter*.—2.4 cm.
*Color of ray florets, upper surface*.—RHS 53A.
*Color of ray florets, lower surface*.—RHS 47A.

Mature inflorescence:
*Diameter*.—4.0 cm.
*Depth*.—1.5 cm.
*Total diameter of disc*.—0.2-0.5 cm.
*Receptacle color*.—RHS 138B.
*Receptacle height*.—0.3 cm.
*Receptacle diameter*.—1.1 cm.
*Length of corolla tube*.—0.2 cm.

Ray florets:
*Average quantity of florets*.—125 in several whorls.
*Color of florets, upper surface*.—RHS 46A.
*Color lower surface*.—RHS 47A.
*Length*.—1.6 cm.
*Width/diameter*.—0.4 cm.
*Shape*.—Oblong.
*Apex shape*.—Rounded, occasionally tridentate.
*Base shape*.—Tube.
*Margin*.—Entire. Small incisions may be present at tip.
*Margin*.—Type of rolling: Flat.
*Texture, upper surface*.—Papillate.
*Lower surface*.—Papillate.
*Ribs present*.—No.
*Number of keels*.—0.
*Profile at widest point*.—Flat.
*Longitudinal axis shape*.—Straight.
*Longitudinal axis curvature strength*.—No curve.
*Corolla tube shape*.—Flattened.

Disc florets:
*Number of disk florets*.—Approximately 20.
*Width*.—0.1 cm.
*Length*.—1.1 cm.
*Colour*.—RHS 17C.

Inflorescence (at moment of senescence):
*Color of ray florets, upper surface*.—RHS 46A.
*Color of ray florets, lower surface*.—RHS 47A.

Phyllaries:
*Quantity*.—22-28.
*Color, upper surface*.—RHS 138B.
*Color, lower surface*.—RHS 138A.
*Length*.—0.4 cm.
*Width*.—0.2 cm.
*Shape*.—Lanceolate.
*Apex shape*.—Acute.
*Base*.—Fused.
*Margins*.—Entire.
*Texture, upper surface*.—Glabrous.
*Texture, lower surface*.—Canescent.

Reproductive organs:
*Pistil*.—One.
*Length*.—0.4 cm.
*Style color*.—RHS 2D.
*Style length*.—0.3 cm.
*Stigma color*.—RHS 16A.
*Stigma shape*.—Bi-parted.
*Ovary color*.—RHS 157B.
*Ovary length*.—0.2 cm.
*Ovary width*.—0.1 cm.

Androecium:
*Stamens*.—1, found on only disc florets.
*Color of filaments*.—RHS 157C.
*Length filaments*.—0.2 cm.
*Anther color*.—RHS 17C.
*Anther length*.—0.2 cm.
*Anther shape*.—Oval to club shaped.
*Color of pollen*.—RHS 17C.
*Pollen amount*.—Sparse.
*Fertility/seed set*.—Has not been determined to date.
*Disease/pest resistance*.—Has not been determined to date.
*Hardiness*.—Has not been determined to date.

What is claimed is:

1. A new and distinct variety of *Chrysanthemum* plant named 'CIFZ0097' substantially as illustrated and described herein.

* * * * *